(12) United States Patent
Park et al.

(10) Patent No.: US 10,842,468 B2
(45) Date of Patent: Nov. 24, 2020

(54) APPARATUS FOR COLLECTING SAMPLE OF VAGINAL SECRETION CONTAINING CERVICAL CELLS

(71) Applicant: TCM BIOSCIENCES INC., Seongnam-si (KR)

(72) Inventors: Young Chui Park, Seoul (KR); Hee Jae Joo, Yongin-si (KR); Dong Jin Shin, Seongnam-si (KR)

(73) Assignee: TCM BIOSCIENCES INC., Gyeonggi-Do (KR)

( * ) Notice: Subject to any disclaimer, the term of this patent is extended or adjusted under 35 U.S.C. 154(b) by 0 days.

(21) Appl. No.: 15/561,995

(22) PCT Filed: Jul. 12, 2017

(86) PCT No.: PCT/KR2017/007463
§ 371 (c)(1),
(2) Date: Sep. 27, 2017

(87) PCT Pub. No.: WO2018/207970
PCT Pub. Date: Nov. 15, 2018

(65) Prior Publication Data
US 2020/0100772 A1 Apr. 2, 2020

(30) Foreign Application Priority Data
May 8, 2017 (KR) .......................... 10-2017-0057572

(51) Int. Cl.
*A61B 10/00* (2006.01)
(52) U.S. Cl.
CPC .. *A61B 10/0045* (2013.01); *A61B 2010/0074* (2013.01)

(58) Field of Classification Search
CPC .................. A61B 10/0045; A61B 2010/0074
See application file for complete search history.

(56) References Cited

U.S. PATENT DOCUMENTS

| 4,475,911 A | * | 10/1984 | Gellert | ............... A61F 13/2037 604/367 |
| 4,769,924 A | * | 9/1988 | Hikota | ................... D06B 15/04 15/309.2 |

(Continued)

FOREIGN PATENT DOCUMENTS

| JP | 2002372527 A | 12/2002 |
| KR | 100524665 B1 | 11/2005 |

(Continued)

OTHER PUBLICATIONS

Merriam Webster Dictionary website, retrieved Jun. 10, 2020 (Year: 2020).*

(Continued)

*Primary Examiner* — Daniel L Cerioni
*Assistant Examiner* — Raymond P Dulman
(74) *Attorney, Agent, or Firm* — Caesar Rivise, PC

(57) ABSTRACT

Disclosed herein is a sample collection apparatus. The sample collection apparatus includes a self-sampling pad and a cell fixing container, wherein the sample collection pad includes a filter unit, the structure and material of which are such that cells, viruses and DNAs contained in vaginal secretions can be efficiently absorbed and attached to the filter unit and can be efficiently detached from the filter unit in a cell preserving solution after the filter unit is removed and put into the cell preserving solution. Thus, the filter unit includes at least one adsorbent layer which is formed of a hydrophobic material having low fineness and high resilience.

11 Claims, 3 Drawing Sheets

(56) References Cited

U.S. PATENT DOCUMENTS

| | | | | |
|---|---|---|---|---|
| 4,794,034 | A | * | 12/1988 | Nishizawa ................ B32B 5/26 428/218 |
| 4,865,596 | A | * | 9/1989 | Weisman ................ A61F 13/53 604/368 |
| 2003/0039833 | A1 | * | 2/2003 | Sen .......................... D01F 6/46 428/373 |
| 2005/0241095 | A1 | * | 11/2005 | Olson .................... A47L 13/16 15/228 |
| 2006/0207296 | A1 | * | 9/2006 | Fujikawa ............. A47C 31/006 66/202 |
| 2008/0069845 | A1 | * | 3/2008 | Makihara .............. D04H 1/498 424/401 |
| 2008/0070282 | A1 | * | 3/2008 | Hwang ................ C12Q 1/6806 435/91.2 |
| 2009/0004435 | A1 | * | 1/2009 | Hanao .................... A61F 13/53 428/156 |
| 2015/0203997 | A1 | * | 7/2015 | Yamanaka ............... D03D 1/00 2/97 |
| 2017/0102399 | A1 | * | 4/2017 | Mamenta ............... G01N 33/80 |
| 2017/0202542 | A1 | * | 7/2017 | Park ................... A61B 10/0045 |

FOREIGN PATENT DOCUMENTS

| | | |
|---|---|---|
| KR | 20060001380 A | 1/2006 |
| KR | 1020090033644 | 3/2010 |
| KR | 20110056648 A | 5/2011 |
| KR | 1020110056648 | 7/2011 |
| WO | 2003009798 A2 | 2/2003 |
| WO | 2007052427 A1 | 5/2007 |

OTHER PUBLICATIONS

Birtwistle, Fern, STIC Search Results, received Mar. 26, 2020 (Year: 2020).*

KR Patent Application No. 10-2017-7025575, Notice of Submission of Opinion, dated Dec. 15, 2017.

KR Patent Application No. 10-2017-7025575, the Final Decision for Registration, dated Sep. 10, 2018.

* cited by examiner

[FIG. 1]
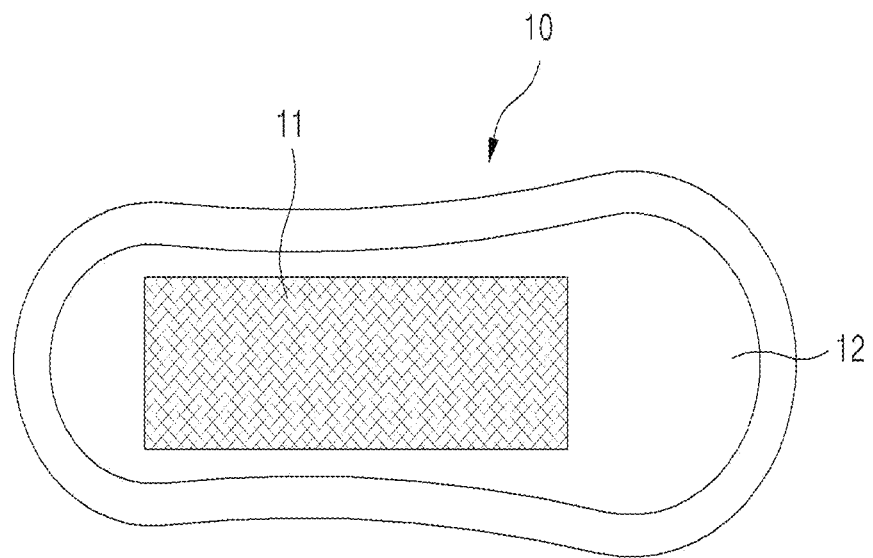
[FIG. 2]
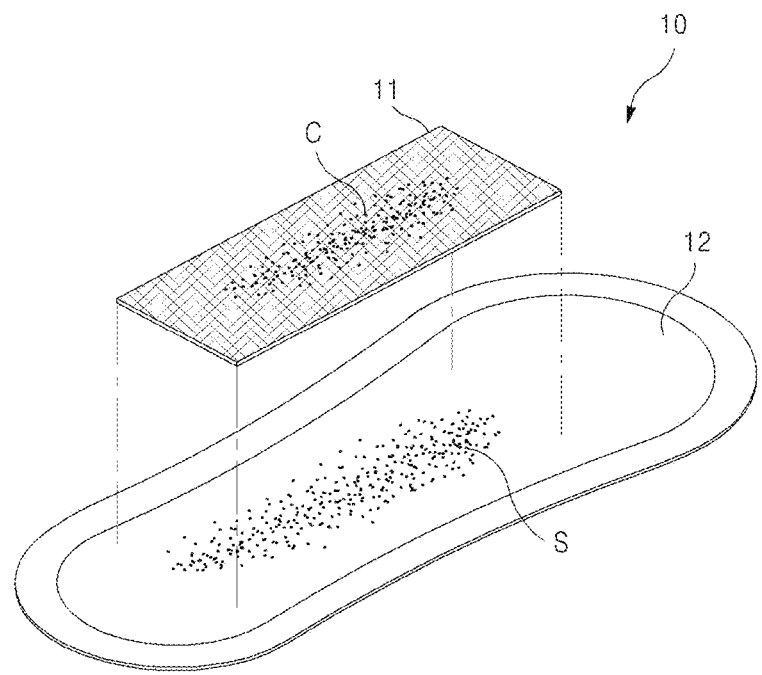

[FIG. 3]
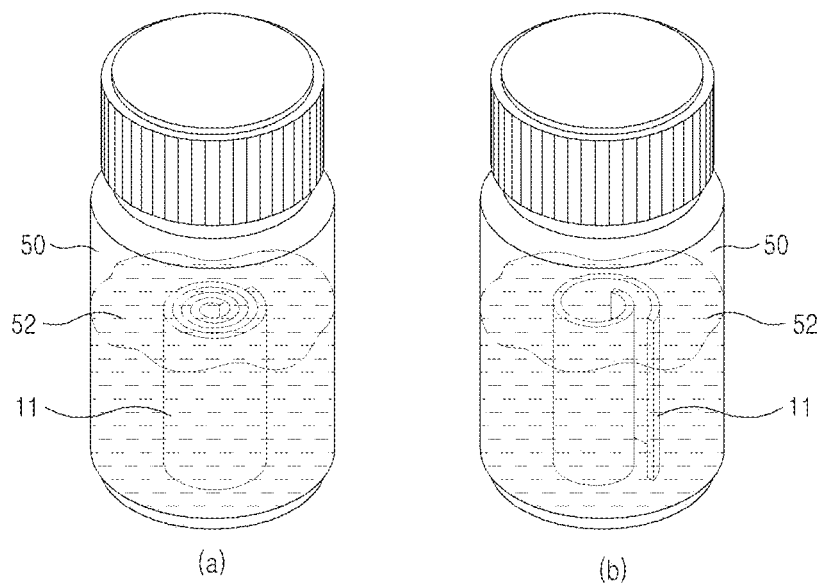
[FIG. 4]
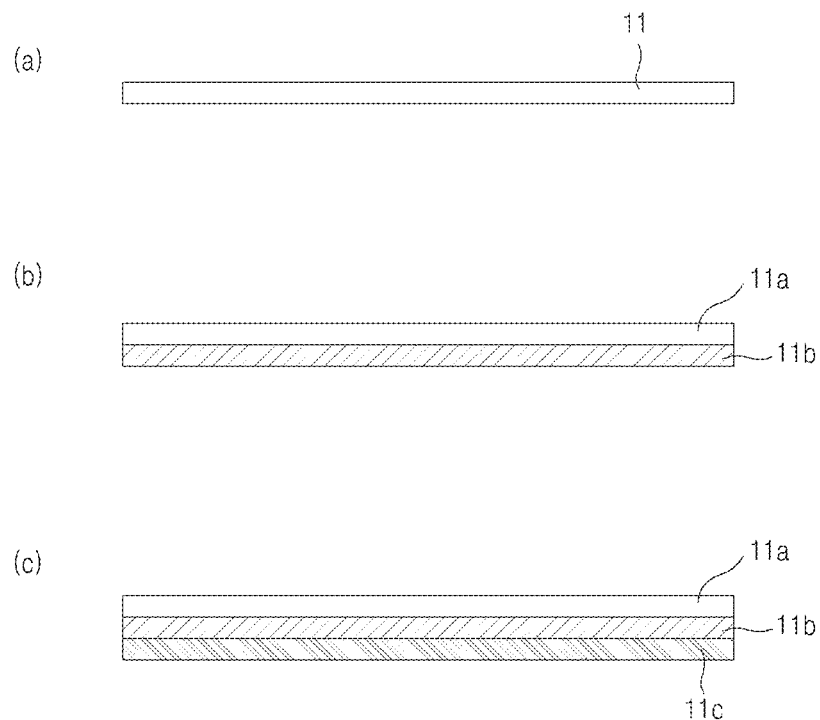

【FIG. 5】
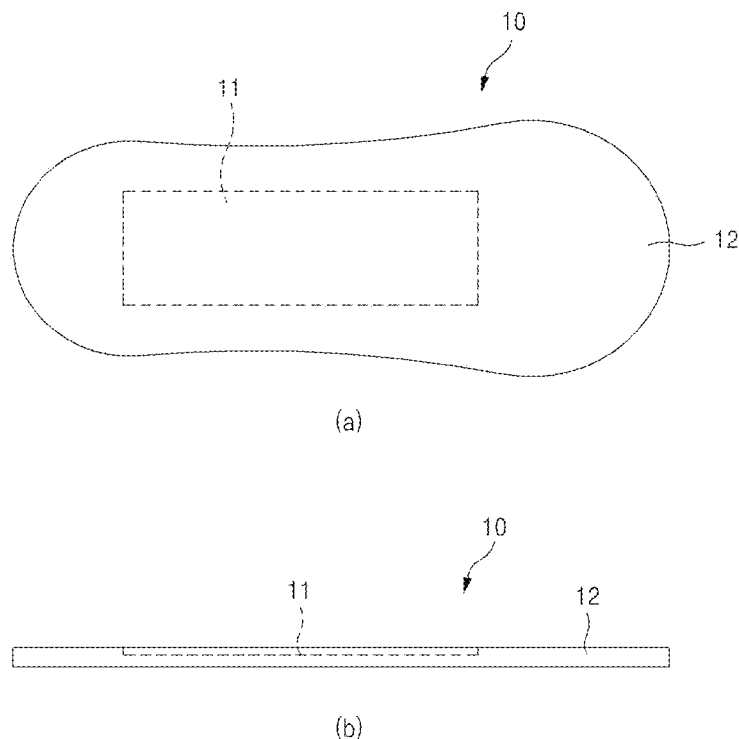
(a)
(b)
【FIG. 6】
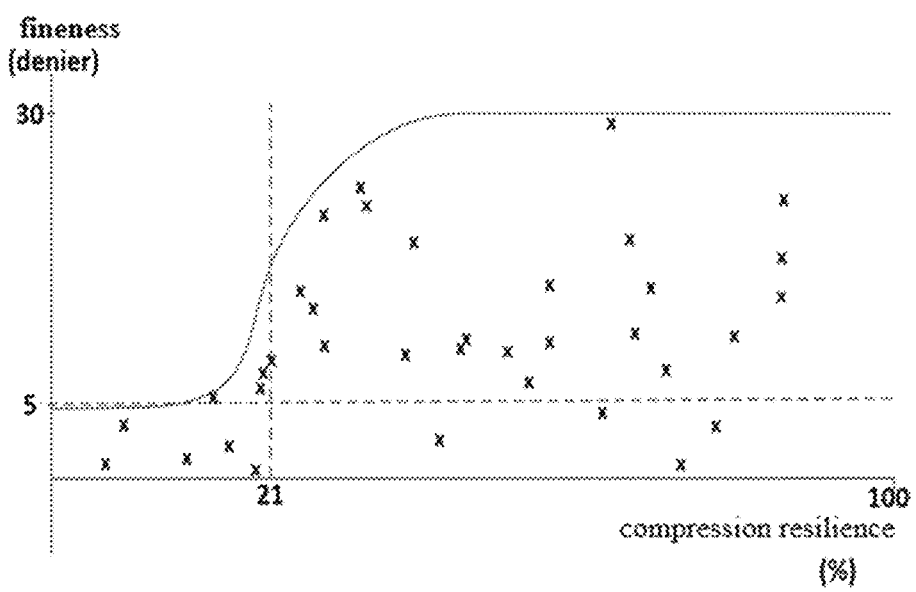

APPARATUS FOR COLLECTING SAMPLE OF VAGINAL SECRETION CONTAINING CERVICAL CELLS

FIELD OF THE DISCLOSURE

The present invention relates to a sample collection apparatus configured to self-sampling of vaginal secretions containing cervical cells that will be sent to a health screening institution such as a clinical/commercial laboratory and used for screening for female diseases, particularly, cervical diseases.

BACKGROUND

The uterus is composed of the corpus and the cervix, and uterine cervical cancer refers to a malignant tumor arising from the uterine cervix connected to the vagina. Uterine cervical cancer is the world's second most common type of cancer in women. It is known that about 85% of cervical cancer cases occur in developing countries in Asia, South America, and Africa.

Uterine cervical cancer, one of the most common forms of cancer in women, is a tumor, pathogenesis of which is relatively well known, and is caused by the human papilloma virus. When epithelial cells of the female genitalia are infected with the human papilloma virus during sexual intercourse, DNA of the human papilloma virus penetrates the cell nucleus and proliferates, causing epidermoid carcinoma. Although detection of human papilloma virus infection has been performed by various methods including cervical Pap smear, polymerase chain reaction (PCR) examination is considered the most sensitive and accurate among screening methods for early diagnosis of uterine cervical cancer. PCR examination is sensitive enough to accurately detect uterine cervical cancer using a single cell. However, for this examination, uterine cervical cells must be collected. For this, a woman needs to go to the hospital and allow a doctor to take cervical cells from her genitalia, which is a burden on her in terms of time and costs as well as causes her to feel embarrassment due to the fact that she reveals her genitals to a clinician.

In addition, a typical instrument for collecting uterine cervical cells like brush or spatula is pointed at an end of a cell collection portion thereof and thus can hurt the vaginal wall or the uterine cervix, which can cause secondary infection, even when a skilled doctor collects uterine cervical cells using the instrument.

In order to solve these problems, the present applicant developed a pad for self-collection of vaginal secretions containing cervical cells (Korean Patent No. 10-524665 and PCT/KR2014/009286). Such a self-collection pad is configured to be attached to underpants of a woman to be wearable for a certain period of time. Then, a filter unit with vaginal secretions absorbed thereby is separated from the pad, put into a kit containing a cell preserving solution, and sent to a health screening institution (for example, a hospital or a clinical/commercial laboratory). In the health screening institution, the cell preserving solution is subjected to centrifugation, followed by detection of infection with HPV or STDs by the molecular analysis methods such as PCR method.

In order to provide more reliable test results, it is required that cells, viruses, and DNA contained in vaginal secretions be efficiently absorbed and attached to the filter unit of the self-sampling pad and, after the filter unit is separated and put into the cell preserving solution, the cells, viruses, and DNA be efficiently detached from the filter unit in the cell preserving solution.

Therefore, there is a need for a filter unit capable of providing the aforementioned functions.

The present invention has been conceived to solve such problems in the art and it is an object of the present invention to provide a sample collection apparatus which includes a filter unit allowing cells, viruses and DNA contained in vaginal secretions to be efficiently absorbed and attached thereto, and allowing the cell preserving solution, the cells, viruses, and DNA to be efficiently detached therefrom in the cell preserving solution after the filter unit is separated and put into a cell preserving solution.

It is another object of the present invention to provide a sample collection apparatus which includes a filter unit that can be easily taken off or separated by a simple operation by a user to improve productivity of the sample collection apparatus while reducing production costs thereof.

BRIEF SUMMARY

In accordance with an aspect of the present invention, a sample collection apparatus includes: a filter unit collecting vaginal secretions containing cervical cells, the filter unit being removed and put into a cell preserving solution after collection of the vaginal secretions; and an absorption unit absorbing the vaginal secretions having passed through the filter unit, wherein the filter unit comprises at least one adsorbent layer formed of a material having a fineness (y) and a compression resilience (x) which are the y value and the x value located below the line of a curve represented by the following Equation 1 on an x-y graph, $$y = 5 + 25\left(\frac{1}{1 + e^{-0.37(x-21)}}\right)$$

(where y denotes the fineness (unit: denier) of fibers, and x denotes the compression resilience (unit: %) of the adsorbent layer.).

The material may exhibit hydrophobicity when the fineness is less than or equal to 5.1 denier.

The adsorbent layer may have a compression resilience of 50% or more when the fineness exceeds 5.1 denier.

The adsorbent layer may be formed of a hydrophobic material having a standard moisture regain of 5% or less.

The adsorbent layer may be formed of polyester, polyolefin, polyamide, polyacrylic fibers, or mixtures thereof.

The filter unit may further include a water permeable layer formed of a hydrophilic material on the adsorbent layer, wherein the water permeable layer is formed of rayon, cotton, pulverized wood pulp, wool, silk, or cellulosic fibers and has pores having a pore size of 0.1 mm to 1 mm.

The filter unit may further include a support layer formed of a material having higher strength and elasticity than the adsorbent layer under the adsorbent layer, wherein the support layer has a mesh structure.

The sample collection apparatus may further include: a cell fixing container to preserve the filter unit having been removed, wherein the cell fixing container contains a cell preserving solution composed of a polar solvent.

The cell preserving solution may be obtained by mixing an alcoholic solution with a solution capable of optimizing a polymerase chain reaction. Examples of the alcoholic solution may include ethanol, methanol, and the like, and examples of the solution capable of optimizing a polymerase chain reaction may include a PBS buffer solution, paraformaldehyde, and the like.

The filter unit of the sample collection apparatus may be formed as a surface layer of the absorption unit and may be provided with a perforated line to facilitate separation of the filter unit from the absorption unit.

According to the present invention, the sample collection apparatus includes a filter unit allowing cells, viruses and DNA contained in vaginal secretions to be efficiently absorbed and attached thereto, and allowing the cell preserving solution, the cells, viruses, and DNA to be efficiently detached therefrom in the cell preserving solution after the filter unit is separated and put into a cell preserving solution, thereby improving reliability of cervical disease screening.

In addition, the filter unit of the sample collection apparatus includes can be easily taken off or separated by a simple operation by a user, thereby improving productivity of the sample collection apparatus while reducing production costs thereof.

BRIEF DESCRIPTION OF THE DRAWINGS

FIGS. 1 to 5 are views of a sample collection apparatus according to one embodiment of the present invention.

FIG. 6 is a graph showing requirements for a filter unit of the sample collection pad according to the embodiment of the present invention.

DETAILED DESCRIPTION

Hereinafter, embodiments of the present invention will be described with reference to the accompanying drawings.

FIGS. 1 to 5 are views of a sample collection apparatus according to one embodiment of the present invention. A sample collection apparatus according to the present invention includes: a self-sampling pad 10 which is wearable like a sanitary napkin to self-collect vaginal secretions containing cervical cells; and a cell fixing container 50 containing a cell preserving solution 52 to preserve a filter unit 11 removed from the self-sampling pad and intended to be sent to a clinical/commercial laboratory.

Referring to FIGS. 1 to 3, cervical cells C are naturally shed from the uterine cervix, and the separated cervical cells C are mixed with vaginal secretions S and discharged from the vagina. When the discharged cervical cells C and vaginal secretions S reach the filter unit 11, the liquid vaginal secretions composed of fine particles pass through the filter unit 11 and are absorbed by an absorption unit 12, whereas the cervical cells C greater in size than grids of the filter unit 11 are left behind in the filter unit 11 without passing through the filter unit 11. In other words, cervical cells are collected on the filter unit due to size difference between vaginal secretion particles and cervical cells.

Thereafter, the filter unit 11 is removed from the absorption unit 12 for fixation of the collected vaginal secretions containing cervical cells and then put into the cell fixing container 50 containing the cell preserving solution 52.

As shown in FIGS. 1 and 2, the self-sampling pad 10 according to the present invention may include: the filter unit 11 composed of grids sized to allow vaginal secretions to pass therethrough while preventing cervical cells from passing therethrough; and the absorption unit 12 placed under the filter unit 11 and absorbing vaginal secretions having passed through the filter unit 11. In addition, the self-sampling pad 10 may further include a sheet unit (not shown) configured to support the filter unit 11 and the absorption unit 12 and formed of a water impermeable material to prevent the absorbed vaginal secretions from leaking out.

Further, the sample collection apparatus for cervical disease screening according to the present invention includes the cell fixing container 50 containing the cell preserving solution 52 to store the filter unit 11 having been removed from the self-sampling pad.

The absorption unit 12 absorbing vaginal secretions having passed through the filter unit 11 may be formed of a highly absorbent material in order to effectively absorb the vaginal secretions having passed through the filter unit 11. For example, the absorption unit may be formed of cotton, pulp, or a combination thereof. Specifically, the absorption unit may be formed of pulp and a non-woven fabric (Airlaid) having a sufficient space to absorb and store vaginal secretions. In addition, it is desirable that the absorption unit 120 take the form of a pad that is thinner than commercially available female pads, considering that the amount of vaginal secretions is smaller than that of menstrual fluids.

Here, the sample collection pad 100 may include only the filter unit 11 and the absorption unit 12, or may further include the sheet unit (not shown) depending upon physical conditions of a user and the amount of vaginal secretions.

For preservation of the sample collection pad 10, the self-sampling pad may include an adhesive member attached to a rear surface of the absorption unit 12 when the self-sampling pad 100 is composed of the filter unit 11 and the absorption unit 12, or attached to a rear surface of the sheet unit when the sample collection pad is composed of the filter unit 11, the absorption unit 12, and the sheet unit. For example, the adhesive member may be bonded to an inner surface of a wearer's underpants such that the sample collection pad 10 can remain fixed for a period of time for which vaginal secretions including cervical cells are collected.

The sheet unit is formed of a water impermeable material which allows moisture to be discharged therethrough, but does not allow water to be discharged therethrough to prevent absorbed vaginal secretions from escaping. As a material having this feature, a cover made of a breathable polyethylene film may be used. The sheet unit has a size greater than or equal to that of the absorption unit 12 and is fused to the absorption unit 12 at an edge thereof.

The cell preserving solution 52 may be an alcoholic solution or a solution obtained by mixing an alcoholic solution with a solution capable of optimizing a polymerase chain reaction. Examples of the alcoholic solution include ethanol, methanol, and the like, and examples of the solution capable of optimizing a polymerase chain reaction include a PBS buffer solution, paraformaldehyde, and the like.

The structure and material of the filter unit 11 of the sample collection pad 10 according to the present invention are required to allow cells, viruses and DNA contained in vaginal secretions to be efficiently absorbed and attached to the filter unit and to be efficiently detached from the filter unit in the cell preserving solution after the filter unit is removed and put into the cell preserving solution.

Thus, the filter unit 11 may include at least one adsorbent layer. Preferably, the adsorbent layer is a fabric made of natural or synthetic fibers having low fineness. More preferably, the adsorbent layer is formed of hydrophobic fibers.

The adsorbent layer formed of fibers having low fineness can provide fine adsorption spaces. Particularly, the adsorbent layer formed of hydrophobic fibers allows water contained in vaginal secretions to be efficiently diffused through micro-pores of the fibers while allowing cells, viruses and DNA to be efficiently adsorbed in fine spaces between the fibers due to capillary action. In addition, when the adsorbent layer formed of hydrophobic fibers is immersed in the cell preserving solution mainly composed of alcohol (ethanol or the like), the alcohol, which is a polar solvent, is efficiently diffused through the micro-pores of the fibers without being absorbed by the hydrophobic adsorbent layer. Thus, when the filter unit having been removed from the self-sampling pad, put into the cell fixing container, and sent to a clinical/commercial laboratory is subjected to a vortex process, the cells, viruses, and DNA can be efficiently detached from the filter unit. Such an advantage of the hydrophobic material is more prominent when fibers constituting the adsorbent layer have lower fineness (smaller thickness).

After the self-sampling pad is worn by a user for a certain period of time, the filter unit having vaginal secretions absorbed thereby is removed from the self-sampling pad and rolled or folded and then put into the cell fixing container containing the cell preserving solution to be sent to a clinical/commercial laboratory, as shown in FIG. 3. When the filter unit is rolled or folded, pressure is applied to the adsorbent layer, whereas, after the filter unit is put into the cell fixing container or when the filter unit is subjected to a vortex process, the pressure applied to the adsorbent layer is released (FIG. 3(b)). If fibers constituting the adsorbent layer have high resilience, cells, viruses, and DNAs adsorbed in spaces between the fibers can be easily detached due to resilient force of the fibers when the pressure applied to the adsorbent layer is released during immersion in the cell preserving solution.

Herein, "resilience" refers to a property of a material that enables the material to return to the original shape or position thereof after being bent, stretched, or compressed, and basically has relevance to the elasticity or form of fiber. In addition, as the thickness of fiber increases (i.e., the fineness of fiber increases), a value of resilience becomes higher. Although a low fineness of the adsorbent layer is desirable in terms of adsorption of cells, as described above, a higher fineness of the adsorbent layer is more desirable in terms of detachment of cells in the cell preserving solution due to the resilient force.

Accordingly, the present inventors found requirements of the adsorbent layer to allow cells in vaginal secretions to be efficiently absorbed and attached to the filter unit and to allow the cells to be efficiently detached from the filter unit in the cell preserving solution after the filter unit is removed and immersed in the cell preserving solution.

Preferably, the adsorbent layer is formed of fibers having a fineness lower than a curve of the following equation and a compression resilience, wherein y and x satisfy Equation 1: (Preferably it is made of a fiber having a fineness lower than the y value in the following formula (1) and having a compression resilience higher than x value in the following formula (1)).

$$y = 5 + 25\left(\frac{1}{1 + e^{-0.37(x-21)}}\right) \quad \text{<Equation 1>}$$

In Equation 1, y denotes the fineness (unit: denier) of fibers constituting the adsorbent layer, and x denotes the compression resilience (unit: %) of the adsorbent layer.

From the results of Examples shown in Tables 1 and 2, it can be seen that when the adsorbent layer of the filter unit is formed of fibers having a fineness and a compression resilience higher than the curve of the above-mentioned Equation 1, the adsorbent layer has a relatively low DNA collection rate.

In the graph of FIG. 6, the curve is a curve expressed by Equation 1, and the dots denote samples having a DNA collection rate of 70% or more among samples of Examples shown in Tables 1 and 2. In Tables 1 and 2, Samples 18, 20, 23, 25, 29, 35, 37, 40, 43, 46, 48, 51, 54, 55, 58, and 59 are samples having a fineness and a compression resilience which are located above the curve of the equation (1) in. FIG. 6 (That is, it can be described as being on the left, side of the curve of the equation (1) in FIG. 6). It can be seen that these samples have a relatively low DNA collection rate, as compared with that of samples below the curve of FIG. 6.

Referring to FIG. 6, it is desirable that the adsorbent layer of the filter unit according to the present invention have fineness and compression resilience values located on the below of the curve of FIG. 6, representing Equation 1. In other words, it is desirable that the adsorbent layer be formed of a material having a fineness lower than y and a compression resilience higher than x.

In addition, it is more desirable that the adsorbent layer of the filter unit according to the present invention have a compression resilience of 50% or more when the fineness of the adsorbent layer exceeds 5.1 denier.

In addition, the adsorbent layer of the filter unit may be formed of a hydrophobic material. Examples of hydrophobic fibers include synthetic fibers such as polyester, polyolefin, polyamide, and polyacryl, and mixtures thereof. Alternatively, the hydrophobic fibers may be obtained by imparting hydrophobicity to hydrophobic fibers through, for example, a suitable coating process.

In Tables 1 and 2, Samples 4, 7, 9, 11, and 14 were formed of a hydrophilic material having high standard moisture regain (SMR) and had a significantly lower DNA collection rate than the other samples.

From the results of Examples shown in Tables 1 and 2, it can be seen that the effect of the hydrophobic material on the DNA collection rate was significant only when the fineness of fibers constituting the adsorbent layer was less than or equal to 5.1 denier. In addition, it can be seen that, when the fineness of the fibers was higher than 5.1 denier, even samples having high standard moisture regain also exhibited a DNA collection rate of 70% or more. Accordingly, it is desirable that fibers constituting the adsorbent layer have hydrophobicity when the fineness of the adsorbent layer is less than or equal to 5.1 denier.

Preferably, the hydrophobic material has a standard moisture regain of 7% or less, more preferably 5% or less.

Although the filter unit 11 of the self-sampling pad 10 may be composed of the adsorbent layer alone, it is more desirable that the filter unit further include a water permeable layer 11a formed on the adsorbent layer 11b, as shown in FIGS. 4 (b) and (c).

The water permeable layer 10a serves to aid absorption of vaginal secretions and may be formed of a hydrophilic material. Examples of hydrophilic fibers may include fibers commonly used as absorbers, such as rayon (including typical normal rayon and modified rayon), cotton, pulverized wood pulp, wool, silk, chemically modified, manipulated, or cross-linked cellulosic fibers, synthetic fibers, tissues, and peat moss. These fibers may be used as a mixture thereof. More preferably, the water permeable layer is a nonwoven fabric prepared using the hydrophilic fibers. In addition, it is desirable that the water permeable layer have pores having a pore size of 0.1 mm to 1 mm to facilitate penetration and absorption of vaginal secretions. Further, the water permeable layer may be configured to filter out large cells.

Referring to FIG. 4(c), the filter unit according to the present invention may include a support layer 11c formed under the adsorbent layer 11b. Preferably, the support layer 11c is formed of fibers having higher strength and elasticity than the adsorbent layer in order to support the adsorbent layer 11b having low fineness and high resilience. In addition, it is desirable that the support layer 11c have a fine mesh structure. Further, the support layer 11c may be formed of polyethylene or polypropylene.

Specifically, the support layer has a high strength and high elasticity mesh structure and is bonded to the adsorbent layer, which has low fineness and is likely to exhibit high fluidity in vaginal secretions or the cell preserving solution, to support the adsorbent layer. In addition, the support layer serves to help the filter unit having been rolled or folded and put into the cell fixing container to be easily released such that cells, viruses, and DNAs can be efficiently detached from the filter unit.

Referring to FIG. 5, as an alternative, the self-sampling pad according to the present invention may have a structure in which the filter unit 11 is formed as a surface layer of the absorbent unit 12 rather than being attached to an upper surface of the absorbent unit 12. In this case, a perforated line may be provided to the surface layer to facilitate separation of the filter unit. Further, it is desirable that the surface layer be further provided at a portion of the perforated line with a separation portion to easily initiate separation of the filter unit.

Next, the present invention will be described in more detail with reference to examples.

Example

Samples of materials (Samples 1 to 60) capable of constituting the adsorbent layer of the filter unit were provided, followed by measurement of the fineness, compression resilience (RC), and standard moisture regain (SMR) of each of the samples.

After the length and weight of fibers were measured, based on standard length and unit weight specified in the provided samples, fineness (unit: denier) of each of the samples was calculated according to Equation 2:

$$D = \{\text{standard length } (L)/\text{unit weight } (W)\} \times \{\text{weight of fiber } (w)/\text{length of fiber } (l)\} \quad \text{<Equation 2>}$$

Compression resilience of each of the samples was measured 5 times using a KES-FB system. Measured compression resilience values were averaged based on measurement data with a standard deviation of 10 or less. Results are shown in Tables 1 and 2. Specifically, the compression resilience of each of the samples was measured 5 times under a maximum pressure (Pm) of 500 gf/cm$^2$ at measurement intervals of 10 seconds or less for a given portion of the sample using a cylinder having a diameter of 2 cm as a presser foot. In addition, the thickness of each of the samples was measured under a load of 0.5 gf.

Standard moisture regain of each of the samples was measured after the sample was dried and allowed to stand in a standard test chamber (at 20±2° C. and 65% RH) to have constant weight.

E. coli were used as a microorganism specimen for measurement of DNA collection rate.

Specifically, 2 ml LB medium was inoculated with E. coli, followed by primary cultivation at 37° C. at 250 rpm for 8 hours. Then, 200 μl of the primarily cultivated E. coli was added to 70 ml LB medium, followed by secondary cultivation at 37° C. at 250 rpm for 16 hours, thereby preparing an E. coli culture having a concentration of 3-4×10$^9$ cells/ml. Then, 30 ml of ethanol was added to the culture, thereby obtaining inactivated E. coli.

A filter unit was placed on each of 10 hand towels, followed by application of 1 ml of the inactivated E. coli to the filter unit, which, in turn, was allowed to stand at room temperature for 10 hours.

Thereafter, the filter unit was rolled and put into a container containing 20 ml of phosphate buffered saline (PBS) including 30% ethanol and then allowed to stand for 48 hours.

After the container containing the filter unit was vortexed at full speed for 1 minute, 12.5 ml of the PBS solution was transferred into a 15-ml tube, followed by centrifugation at 2500 rpm at room temperature for 10 minutes. After removal of a supernatant, 1 ml of PBS was added to the container, followed by resuspension, and then centrifugation was performed at 10,000 g for 1 minute, thereby obtaining a precipitate. Then, the precipitate was subjected to DNA extraction using Exgene™ Clinic SV kit (GeneAll, Korea), thereby finally acquiring 200 μl of E. coli gDNA.

The DNA concentrations were measured using an Epoch™ multi-volume spectrophotometer system (BioTek, USA) and three independent tests was conducted.

Here, an E. coli DNA collection rate (%) was calculated as a ratio of DNA concentration per 1 ml of E. coli culture after the above procedure to DNA concentration per 1 ml of E. coli before filtration, and results were averaged to determine the DNA concentration rate, based on data with a standard deviation of 20(%) or less. Results are shown in Tables 1 and 2.

TABLE 1

| Sample | Fineness (denier) | RC (%) | SMR (%) | E. coli DNA Collection Rate (%) |
|---|---|---|---|---|
| 1 | 0.5 | 18 | 0.9 | 78 |
| 2 | 0.62 | 5 | 0.7 | 76 |
| 3 | 0.9 | 78 | 1.2 | 83 |
| 4* | 1.0 | 42 | 12.0 | 52 |
| 5 | 1.5 | 13 | 2.1 | 77 |
| 6 | 2.3 | 17 | 1.5 | 76 |
| 7* | 2.9 | 49 | 10.0 | 47 |
| 8 | 3.0 | 37 | 2.0 | 73 |
| 9* | 3.6 | 41 | 9.8 | 49 |
| 10 | 4.5 | 83 | 3.7 | 80 |
| 11* | 4.5 | 49 | 7.9 | 51 |
| 12 | 4.9 | 7 | 4.5 | 71 |
| 13 | 5.1 | 71 | 0.9 | 78 |
| 14* | 5.1 | 57 | 8.5 | 51 |
| 15 | 5.8 | 16 | 5.0 | 70 |
| 16 | 6.5 | 20 | 5.0 | 71 |
| 17 | 6.9 | 53 | 4.8 | 71 |
| 18* | 7.5 | 16 | 6.3 | 52 |
| 19 | 8.0 | 19 | 3.2 | 70 |
| 20* | 8.2 | 15 | 5.1 | 46 |
| 21 | 8.2 | 74 | 0.8 | 78 |
| 22 | 9.0 | 41 | 6.2 | 74 |
| 23* | 9.5 | 15 | 6.7 | 53 |
| 24 | 9.6 | 21 | 3.0 | 70 |
| 25 | 10.0 | 15 | 4.5 | 50 |
| 26 | 10.0 | 34 | 4.8 | 71 |
| 27 | 10.3 | 45 | 2.1 | 73 |
| 28 | 10.5 | 38 | 1.5 | 70 |
| 29* | 11.0 | 15 | 4.9 | 52 |
| 30 | 11.0 | 56 | 3.0 | 70 |

TABLE 2

| Sample | Fineness (denier) | RC (%) | SMR (%) | E. coli DNA Collection Rate (%) |
|---|---|---|---|---|
| 31 | 11.5 | 48 | 1.2 | 70 |
| 32 | 12.0 | 39 | 4.3 | 70 |
| 33 | 12.3 | 84 | 0.9 | 77 |
| 34 | 12.9 | 69 | 6.2 | 75 |
| 35* | 13.0 | 18 | 5.9 | 53 |
| 36 | 13.5 | 61 | 2.6 | 72 |
| 37* | 14.0 | 16 | 4.8 | 50 |
| 38 | 14.2 | 59 | 1.2 | 75 |
| 39 | 14.5 | 25 | 3.9 | 70 |
| 40* | 14.5 | 16 | 7.0 | 55 |
| 41 | 15.0 | 87 | 1.8 | 80 |
| 42 | 15.1 | 23 | 3.9 | 70 |
| 43* | 16.0 | 18 | 12.0 | 50 |
| 44 | 16.3 | 51 | 1.4 | 76 |
| 45 | 16.9 | 25 | 3.7 | 71 |
| 46* | 17.5 | 19 | 4.3 | 54 |
| 47 | 18.3 | 77 | 1.0 | 84 |
| 48* | 18.9 | 20 | 7.1 | 55 |
| 49 | 19.0 | 34 | 2.1 | 71 |
| 50 | 19.5 | 58 | 0.8 | 74 |
| 51* | 20.0 | 20 | 7.3 | 51 |
| 52 | 21.5 | 26 | 4.3 | 70 |
| 53 | 22.0 | 30 | 1.2 | 71 |
| 54* | 22.1 | 16 | 7.4 | 50 |
| 55* | 22.4 | 21 | 6.5 | 55 |
| 56 | 23.0 | 87 | 2.1 | 82 |
| 57 | 24.5 | 28 | 4.8 | 70 |
| 58* | 27.0 | 20 | 4.3 | 54 |
| 59* | 28.0 | 22 | 5.0 | 55 |
| 60 | 29.6 | 65 | 2.3 | 75 |

As above, the present invention has been described with reference to preferred embodiments in conjunction with the accompanying drawings. Although specific terms have been used herein, it should be understood that these terms are used for illustration only and are not intended to limit the scope of the present invention. Thus, it should be understood that various modifications, variations, and alterations can be made by those skilled in the art without departing from the spirit and scope of the present invention. Therefore, the scope of the invention should be limited only by the accompanying claims and equivalents thereof.

The invention claimed is:

1. A sample collection apparatus, comprising:
a filter unit collecting vaginal secretions containing cervical cells, the filter unit being removed and put into a cell preserving solution after collection of the vaginal secretions; and
an absorption unit absorbing the vaginal secretions having passed through the filter unit,
wherein the filter unit comprises at least one adsorbent layer formed of a material having a fineness (y) and a compression resilience (x) which are the x and y values located below the line of a curve represented by the following Equation 1 on an x-y graph:

$$y = 5 + 25\left(\frac{1}{1 + e^{-0.37(x-21)}}\right)$$

(where y denotes the fineness (unit: denier) of fibers, and x denotes the compression resilience (unit: %) of the fibers), and
the material exhibits hydrophobicity when the fineness is less than or equal to 5.1 denier; and
wherein the at least one adsorbent layer is formed of a hydrophobic material having a standard moisture regain of 5% or less and a DNA collection rate of 70% or more.

2. The sample collection apparatus according to claim 1, wherein the adsorbent layer has a compression resilience of 50% or more when the fineness exceeds 5.1 denier.

3. The sample collection apparatus according to claim 1, wherein the adsorbent layer is formed of polyester, polyolefin, polyamide, polyacrylic fibers, or mixtures thereof.

4. The sample collection apparatus according to claim 1, wherein the filter unit further comprises a water permeable layer formed of a hydrophilic material on the adsorbent layer.

5. The sample collection apparatus according to claim 4, wherein the water permeable layer is formed of rayon, cotton, pulverized wood pulp, wool, silk or cellulosic fibers.

6. The sample collection apparatus according to claim 4, wherein the water permeable layer has pores having a pore of 0.1 mm to 1 mm.

7. The sample collection apparatus according to claim 1, wherein the filter unit further comprises a support layer formed of a material having higher strength and elasticity than the adsorbent layer under the adsorbent layer.

8. The sample collection apparatus according to claim 1, wherein the filter unit further comprises a support layer having a mesh structure under the adsorbent layer.

9. The sample collection apparatus according to claim 1, further comprising:
a cell fixing container to preserve the filter unit having been removed,
wherein the cell fixing container contains a cell preserving solution composed of polar solvent.

10. The sample collection apparatus according to claim 9, wherein the cell preserving solution is obtained by mixing an alcoholic solution with a buffer solution and formaldehyde.

11. The sample collection apparatus according to claim 1, wherein the filter unit is formed as a surface layer of the absorption unit and is provided with a perforated line to facilitate separation of the filter unit from the absorption unit.

* * * * *